United States Patent [19]

Dickerson

[11] 4,379,940

[45] Apr. 12, 1983

[54] VINYL ACETATE PURIFICATION PROCESS

[75] Inventor: Richard C. Dickerson, Virginia Beach, Va.

[73] Assignee: Ecolochem, Inc., Norfolk, Va.

[21] Appl. No.: 201,373

[22] Filed: Oct. 27, 1980

[51] Int. Cl.$^3$ .................... C07C 67/00; C07C 67/56
[52] U.S. Cl. .................................. 560/248; 560/261
[58] Field of Search ............................. 560/248, 261

[56] References Cited

U.S. PATENT DOCUMENTS

| | | |
|---|---|---|
| 2,409,441 | 5/1946 | Metzger . |
| 2,986,575 | 5/1961 | Hubner ............................ 560/248 |
| 3,235,610 | 3/1966 | Wymore . |
| 3,318,948 | 10/1967 | Burgess . |
| 3,324,156 | 4/1967 | Elder et al. . |
| 3,399,208 | 7/1968 | Ward . |
| 3,438,892 | 7/1969 | Wymore et al. . |
| 3,905,875 | 3/1975 | Kronig et al. . |
| 3,922,217 | 4/1975 | Cohen et al. . |
| 3,969,344 | 3/1976 | Ackermann et al. . |
| 3,985,648 | 1/1976 | Casolo . |
| 4,049,548 | 2/1977 | Dickerson . |
| 4,283,572 | 8/1981 | Klicker ............................ 568/783 |

FOREIGN PATENT DOCUMENTS

| | | | |
|---|---|---|---|
| 45-11484 | 4/1970 | Japan | .................... 560/248 |
| 1125048 | 9/1968 | United Kingdom . | |

OTHER PUBLICATIONS

Rohm & Haas Co., "Amberlyst 15 Synthetic Resin Catalyst Technical Notes," Washington Square, Phila. 5, Pa., pp. 1 and 3, 1962.
Don Chemical Co., "Dowex: Ion Exchange", Midland, Mich., p. 33, 1964.
C. Calmon et al., Ion Exchangers in Organic and Biochemistry, pp. 640–643; pp. 655–657 (1957).
Kirk-Othmer, Encyclopedia of Chemical Technology (2nd Edition), (1966), vol. 11, pp. 871–899; vol. 21, pp. 329–330 (1970).
Industrial Chemicals, Vinyl Acetate, pp. 800–804.
Amberlite IRA-94, Rohm & Haas Company, 1978.
IONAC AFP-329, Ionac Chemical Company.

*Primary Examiner*—Howard T. Mars
*Attorney, Agent, or Firm*—Lane, Aitken & Kananen

[57] ABSTRACT

A process for purifying vinyl acetate contaminated with acetic acid, coloration agents, water, and/or sodium chloride. The first stage consists of removing acetic acid by passing the vinyl acetate feed through a dehydrated anion exchange resin bed. The second stage consists of removing coloration agents by passing the vinyl acetate feed through a bed of activated carbon. The third stage consists of removing water by passing the vinyl acetate feed through a bed of desiccant. The fourth stage consists of removing sodium chloride by passing the vinyl acetate feed through separate cation exchange resin and anion exchange resin beds or through a mixed resin bed.

13 Claims, No Drawings

VINYL ACETATE PURIFICATION PROCESS

BACKGROUND OF THE INVENTION

1. Field of the Invention

The invention is in the field of commercial chemical purification and separation; more particularly, in the field of commercial processes for purifying vinyl acetate monomer which has become impure or contaminated.

2. Description of the Prior Art

Vinyl acetate monomer is commercially prepared from acetylene and acetic acid. The vapor-phase reaction between acetylene and acetic acid in the presence of a zinc acetate catalyst yields vinyl acetate.

Acetylene is specially purified to remove hydrogen sulfide and phosphorus compounds. It is then mixed in slight excess with vaporized acetic acid and fed to a multitubular fixed-bed reactor containing a catalyst of zinc acetate deposited on activated carbon (10 percent Zn). Reaction is exothermic so the reactor is cooled by circulating oil around the tubes. Reactor temperature is maintained at 350° to 400° F. (177° to 204° C.). The reactor effluent is condensed and fed to a light ends column, where acetylene, methyl acetylene, propadiene, and other light ends are removed from the top of the column. The acetylene must be repurified before it may be recycled.

Vinyl acetate is distilled overhead in a vinyl acetate column. Recycle acetic acid is separated from heavy ends in a recovery column.

Vinyl acetate monomer, which has the chemical formula $CH_3COOCH=CH_2$, is supplied commercially in grades which differ in the amount of chemical inhibitor they contain but otherwise have identical specifications. Typical manufacturers' specifications are:

| | |
| --- | --- |
| Vinyl acetate, % | 99.8, min |
| Boiling point, °C. | 72.3–73.0 |
| Acidity as acetic acid, % by wt. | 0.005, max |
| Carbonyls as acetaldehyde, % by wt. | 0.013, max |
| Water, % by wt. | 0.04, max |
| Color APHA system | 0–5 |
| Suspended matter | None |

Despite the use of chemical inhibitors, a significant commercial problem exists in that bulk quantities of vinyl acetate monomer in storage or in transportation tanks frequently build up acetic acid and coloration agents during hot weather due to the heat and the presence of oxygen or metal ions which may cause decomposition of the monomer to form acetic acid and the coloration agents. Another commercial problem which may occur is that vinyl acetate monomer will pick up sodium chloride during shipment or storage.

At the present time, manufacturers of vinyl acetate monomer have specifications of 0.005% by weight acetic acid (max.) and 0.04% by weight water (max.). Furthermore, the monomer should be water white, i.e., have no color, and be free of sodium chloride.

When a bulk quantity of vinyl acetate monomer fails to satisfy the standard specifications because of excess acetic acid, water, sodium chloride, and/or coloration, the monomer either will be sold at a significant discount or it will be re-distilled which is an energy-intensive and, therefore, expensive process.

SUMMARY OF THE INVENTION

The object of the present invention is to provide a low-cost commercial purification process which will solve the problem of excess acetic acid, coloration, water, and/or sodium chloride in bulk quantities of vinyl acetate monomer without the need of expensive re-distillation procedures.

It has now been discovered that excess acetic acid, coloration agents, water, and/or sodium chloride may be removed from bulk quantities of liquid vinyl acetate monomer by a low-cost process. The inventive process consists of one or more stages, depending upon the type of contaminant present in the batch of vinyl acetate monomer.

The first stage uses a dehydrated anion exchange resin bed to remove acetic acid from the vinyl acetate monomer.

If coloration agents are present in the vinyl acetate monomer, the second stage will consist of removing the coloration agents using a bed of activated carbon.

If excess water is present in the vinyl acetate monomer, the third stage will consist of removing the water using a desiccant.

If sodium chloride is present in the vinyl acetate monomer, the fourth stage will consist of removing the sodium chloride using separate cation exchange resin and anion exchange resin beds or a mixed bed of cation exchange resin and anion exchange resin or a combination of separate beds and a mixed bed.

It should be noted that the four stages may be run in any sequence desired. Furthermore, if coloration agents, excess water, and/or sodium chloride are not present in the vinyl acetate monomer, then the second, third, and/or fourth stage will not be used. A batch of contaminated vinyl acetate monomer is chemically analyzed before beginning the purification process in order to determine what contaminants are present and therefore which stages will be employed for the particular batch of monomer.

DESCRIPTION OF THE PREFERRED EMBODIMENTS

The first stage of the inventive process may be performed using either a gel type anion exchange resin or a macroreticular type anion exchange resin. The macroreticular type of anion exchange resin is preferred because of the ability to withstand heating without cracking or fracturing.

In the preferred embodiment of the first stage, the anion exchange resin is subjected to a pre-treatment step consisting of removing water from the resin. The contaminated vinyl acetate monomer is then passed through the bed of the dehydrated anion exchange resin. The acetic acid is removed by the resin and the purified vinyl acetate monomer exits from the bed.

Vinyl acetate monomer is a liquid at standard temperature and pressure. The inventive process will usually be conducted at ambient temperature where vinyl acetate monomer is a liquid. The pressure on the vinyl acetate monomer may be only the pressure that is needed to pump the liquid monomer from a storage facility and through the various beds used in the process. A gravity feed may even be used.

The anion exchange resin used in the first stage will eventually become fully loaded with acetic acid contaminant. The resin will then be regenerated and used again in the purification process.

If coloration agents are present in the vinyl acetate monomer, then the second stage of the process consists of passing the vinyl acetate feed through a bed of activated carbon in order to remove the coloration agents. Any suitable activated carbon may be used for this purpose. An example is Westvaco WVW activated carbon available from Westvaco Corporation.

If excess water is present in the vinyl acetate monomer, then the third stage of the process consists of passing the vinyl acetate feed through a bed of desiccant in order to remove the excess water. Any suitable desiccant may be used for this purpose. An example is silica gel mixed with aluminum sulfate.

If sodium chloride is present in the vinyl acetate monomer, then the fourth stage of the process consists of passing the vinyl acetate feed through separate cation exchange resin and anion exchange resin beds. The sodium ions are removed from the monomer by the cation exchange resin. The chloride ions are removed by the anion exchange resin. Alternatively, a mixed bed of cation and anion exchange resins may be employed or a combination of a mixed bed and separate beds may be employed.

The four stages of the process may be run in any sequence desired. The sequence of the stages is not critical. Furthermore, if coloration agents, excess water, and/or sodium chloride are not present, then the second, third and/or fourth stage will not be run.

Example 1, below, is a teaching example which illustrates one embodiment (not a preferred embodiment) of the first stage of the process. Example 1 uses a gel type strong base anion exchange resin (such as IONAC ASB-1 made by Ionac Chemical Company or AMBERLITE IRA-400 made by Rohm and Haas Company).

EXAMPLE 1

A chromatography tube was packed with 10 cc. of a strong base anion exchange resin in OH form. One liter of vinyl acetate monomer containing 0.03% by weight acetic acid was then passed through the resin.

It was noted during the run that the tube became warm and that some color throw occurred. It was also noted that the vinyl acetate exiting the tube had picked up water from the ion exchange resin. The vinyl acetate was free of acetic acid as shown by the standard bromo thymol blue test procedure for acid.

Example 1 illustrates that gel type strong base anion exchange resins may add color to the vinyl acetate, which is not a desirable result in this process. Thus, it is preferred to use macroreticular type weak base anion exchange resins (Examples 2 and 3, below) in the first stage.

If coloration agents are present in the vinyl acetate, they are removed in a second stage of the process, as described above, by passing the monomer through a bed of activated carbon.

Example 1, above, also illustrates that commercially-available anion exchange resins (which usually contain entrapped or absorbed water) may add water to the vinyl acetate, which is another undesirable result in this process. Thus, it is preferred to pre-treat the commercially-available anion exchange resin in order to remove the water, as will be described below. Otherwise, as in Example 1, some of the water in the resin will enter into the vinyl acetate since water is slightly soluble in vinyl acetate.

If excess water is present in the vinyl acetate monomer, it is removed in a third stage of the process, as described above by passing the monomer through a desiccant which removes the excess water.

Example 2, below, illustrates another embodiment of the first stage of the process wherein an intermediate or weak base anion exchange resin is useful in removing acetic acid contaminant from liquid vinyl acetate monomer. Example 2 also illustrates the use of an organic solvent, methanol (ethanol or ethyl ether can also be used), to pre-treat the ion exchange resin. However, as Example 2 shows, unless the methanol is evaporated from the resin, the water will remain in the resin and will enter into the vinyl acetate.

EXAMPLE 2

A chromatography tube was packed with 10 cc. of a macroreticular weak base anion exchange resin (AMBERLITE IRA-94 made by Rohm and Haas Co.). The resin was flushed with several bed volumes of methanol and then drained.

One liter of vinyl acetate monomer containing 0.03% by weight acetic acid was then passed through the resin. No heating occurred. The vinyl acetate exiting the tube was free of acetic acid and free of color, but it contained excess water (more than 0.04% by weight).

Example 3, below, illustrates one technique of dehydrating the macroreticular weak base anion exchange resin used in the preferred embodiment. The water in the commercially-available weak base anion exchange resin is driven out by heating. It should be noted again that a gel type of anion exchange resin may be used in the first stage process; however, the gel type resin has the disadvantages that it will crack upon heating and it may give off color to the vinyl acetate monomer.

EXAMPLE 3

A quantity (10 cc.) of a macroreticular weak base anion exchange resin (AMBERLITE IRA-94 or IONAC AFP-329 made by Ionac Chemical Co.) was first heated to drive out entrapped water and then packed in a chromatography tube.

One liter of vinyl acetate monomer containing 0.03% by weight acetic acid was passed through the resin. No heating occurred. The vinyl acetate exiting the tube was free of acetic acid, free of color, and it contained less than 0.04% by weight of water.

Another technique of pre-treating to remove the water from the commercially-available anion exchange resin is to flush an organic solvent (such as methanol, ethanol, or ethyl ether) through the resin and drain. This is followed by evaporating the organic solvent using gentle heating. This technique has the advantage of requiring less heat in order to dehydrate the resin.

In commercial practice, the ion exchange resin, the activated carbon, and the desiccant are placed in large cylindrical tanks for performing the purification process. The tanks may be in a mobile purification unit. The teachings of my earlier patent, U.S. Pat. No. 4,049,548 entitled "Mobile Demineralizer" issued Sept. 20, 1977, are incorporated herein by reference to exemplify a mobile purification unit. Alternatively, the tanks may be installed in a permanent site depending upon the particular requirements of the purification task.

The output of the anion exchange resin tank in the first stage of the process is monitored for acid content (e.g., by titration with bromo thymol blue as indicator) in order to determine when the resin needs regeneration. When the resin becomes fully loaded, it is taken out of service for regeneration. For example, a macroreticular weak base anion exchange resin will absorb between 12 to 18 kilograms of contaminants per cubic foot (424 to 635 kilograms of contaminants per cubic meter) of resin before regeneration is necessary.

The vinyl acetate monomer will coat the anion exchange resin beads during the purification process. Therefore, before the anion exchange resin may be regenerated, the vinyl acetate coating must be removed by flushing the resin with an organic solvent (such as methanol, ethanol, or ethyl ether). Then the organic solvent is removed from the resin by flushing the resin with water. Regeneration of the resin may then be performed.

Regeneration of the anion exchange resin is accomplished by using the known methods for each type of resin. For example, a macroreticular weak base anion exchange resin may be regenerated using 3 lbs of a 2-4% sodium hydroxide solution as regenerant per cubic foot of resin (48 kilograms of a 2-4% sodium hydroxide solution as regenerant per cubic meter of resin).

Regeneration also has the effect of re-introducing water into the resin. Therefore, in the preferred embodiment, the pretreatment using an organic solvent such as methanol, ethanol, or ethyl ether is employed again. This is followed by gentle heating to evaporate the organic solvent to remove the water from the resin.

Tests on the effluent from the strong base anion exchange resin bed used in Example 1, above, indicate that the acetic acid was removed from the vinyl acetate monomer by a cation exchange mechanism wherein the acetate ions ($CH_3COO^-$) from acetic acid were exchanged for the hydroxyl ions ($OH^-$) from the resin and that a small amount of water was formed by the hydrogen ions ($H^+$) from acetic acid reacting with the hydroxyl ions ($OH^-$) from the resin.

Tests on the effluent from the macroreticular weak base anion exchange resin bed used in Example 3, above, indicate that the acetic acid was removed from the vinyl acetate monomer by an absorption mechanism.

The above-described embodiments are intended to be illustrative, not restrictive. The full scope of the invention is defined by the claims, and any and all equivalents are intended to be embraced. In interpreting the claims, it is to be understood that the first, second, third, and fourth stages of the process, as described above, may be run in any sequence of order.

I claim:

1. A process for removing acetic acid contaminant from liquid vinyl acetate monomer comprising the following steps:
   (a) providing a bed of a dehydrated anion exchange resin; and
   (b) passing said vinyl acetate monomer containing acetic acid through said anion exchange resin bed whereby said acetic acid contaminant is removed from said vinyl acetate monomer.

2. The process defined in claim 1 wherein said anion exchange resin is dehydrated by heating said resin at a temperature and for a period of time sufficient to remove the water from the resin.

3. The process defined in claim 1 wherein said anion exchange resin is dehydrated by the following steps:
   (1) flushing said resin with an organic solvent; and
   (2) heating said resin at a temperature and for a period of time sufficient to evaporate the organic solvent from the resin.

4. The process defined in claim 3 wherein said organic solvent is selected from the group consisting of methanol, ethanol, and ethyl ether.

5. The process defined in claim 1 wherein said anion exchange resin is an intermediate or weak base anion exchange resin.

6. The process defined in claim 1 wherein said anion exchange resin is a macroreticular weak base anion exchange resin.

7. The process defined in claim 1 comprising the following additional step:
   (c) regenerating said anion exchange resin when said resin has become fully loaded with acetic acid contaminant.

8. The process defined in claim 1 comprising the following additional steps:
   (c) when said anion exchange resin has become fully loaded with acetic acid contaminant, flushing said anion exchange resin with an organic solvent to remove the vinyl acetate coating from said resin; and
   (d) regenerating said anion exchange resin.

9. A process for removing acetic acid contaminant from liquid vinyl acetate monomer comprising the following steps:
   (a) providing a bed of a dehydrated macroreticular weak base anion exchange resin;
   (b) passing said vinyl acetate monomer containing acetic acid through said anion exchange resin bed whereby said acetic acid is removed from said vinyl acetate monomer;
   (c) regenerating said anion exchange resin when said resin has become fully loaded with acetic acid contaminant; and
   (d) dehydrating said regenerated anion exchange resin.

10. A process for removing acetic acid contaminant and coloration agents from liquid vinyl acetate monomer comprising the following steps:
    (a) providing a bed of a dehydrated anion exchange resin;
    (b) passing said vinyl acetate monomer through said anion exchange resin bed whereby said acetic acid contaminant is removed from said vinyl acetate monomer;
    (c) providing a bed of activated carbon; and
    (d) passing said vinyl acetate monomer through said activated carbon bed whereby said coloration agents are removed from said vinyl acetate monomer.

11. A process for removing acetic acid, coloration agents, and excess water from liquid vinyl acetate monomer comprising the following steps:
    (a) providing a bed of a dehydrated anion exchange resin;
    (b) passing said vinyl acetate monomer through said anion exchange resin bed whereby said acetic acid contaminant is removed from said vinyl acetate monomer;
    (c) providing a bed of activated carbon;
    (d) passing said vinyl acetate monomer through said activated carbon bed whereby said coloration agents are removed from said vinyl acetate monomer;
    (e) providing a bed of a desiccant; and
    (f) passing said vinyl acetate monomer through said desiccant bed whereby said excess water is removed from said vinyl acetate monomer.

12. A process for removing acetic acid, coloration agents, excess water, and sodium chloride from liquid vinyl acetate monomer comprising the following steps:
   (a) providing a bed of a dehydrated anion exchange resin;
   (b) passing said vinyl acetate monomer through said anion exchange resin bed whereby said acetic acid contaminant is removed from said vinyl acetate monomer;
   (c) providing a bed of activated carbon;
   (d) passing said vinyl acetate monomer through said activated carbon bed whereby said coloration agents are removed from said vinyl acetate monomer;
   (e) providing a bed of a desiccant;
   (f) passing said vinyl acetate monomer through said desiccant bed whereby said excees water is removed from said vinyl acetate monomer;
   (g) providing separate cation exchange resin and anion exchange resin beds or a mixed resin bed or a combination of separate cation and anion exchange resin beds and a mixed bed; and
   (h) passing said vinyl acetate monomer through said bed or beds defined in step (g) whereby said sodium chloride is removed from said vinyl acetate monomer.

13. The process in claims 10, 11, or 12 wherein the anion exchange resin in step (a) is dehydrated macroreticular weak base anion exchange resin.

* * * * *